United States Patent
Kumasaka

(10) Patent No.: US 6,482,195 B1
(45) Date of Patent: Nov. 19, 2002

(54) DISPOSABLE GARMENT

(75) Inventor: Yoshinori Kumasaka, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/626,382

(22) Filed: Jul. 26, 2000

(30) Foreign Application Priority Data

Jul. 27, 1999 (JP) .......................... 11-212549

(51) Int. Cl.[7] ........................ A61F 13/15; A61F 13/20
(52) U.S. Cl. ..................... 604/385.27; 604/385.21; 604/385.25; 604/385.26
(58) Field of Search .................. 604/385.24–385.3, 604/393–396; 2/400–408

(56) References Cited

U.S. PATENT DOCUMENTS

| | | | |
|---|---|---|---|
| 4,743,241 A | | 5/1988 | Igaue et al. |
| 5,055,103 A | * | 10/1991 | Nomura et al. ......... 604/385.29 |
| 5,334,152 A | * | 8/1994 | Nomura et al. ......... 604/385.29 |
| 5,368,584 A | * | 11/1994 | Clear et al. ............ 604/385.29 |
| 5,447,508 A | | 9/1995 | Numano et al. |
| 5,634,917 A | * | 6/1997 | Fujioka et al. ......... 604/385.29 |
| 5,645,543 A | * | 7/1997 | Nomura et al. ............. 604/396 |
| 5,649,919 A | | 7/1997 | Roessler et al. |
| 5,745,922 A | | 5/1998 | Rajala et al. |
| 5,779,689 A | | 7/1998 | Pfeifer et al. |

FOREIGN PATENT DOCUMENTS

| | | |
|---|---|---|
| JP | 62-231005 | 10/1987 |
| WO | 00/02511 | 1/2000 |

\* cited by examiner

*Primary Examiner*—Glenn K. Dawson
*Assistant Examiner*—K. M. Reichle
(74) *Attorney, Agent, or Firm*—Clark & Brody

(57) ABSTRACT

A disposable garment is provided with leg-hole elastic members, which include first elastic members extending along transversely opposite side edges in a longitudinally middle zone of the garment, second elastic members extending in continuity with the first elastic members toward a front end of the garment and third elastic members extending in continuity with the first elastic members toward a rear end of the garment, and these elastic members have their values of stretch stress in the relationship of the first elastic members>the third elastic members>the second elastic members.

4 Claims, 5 Drawing Sheets

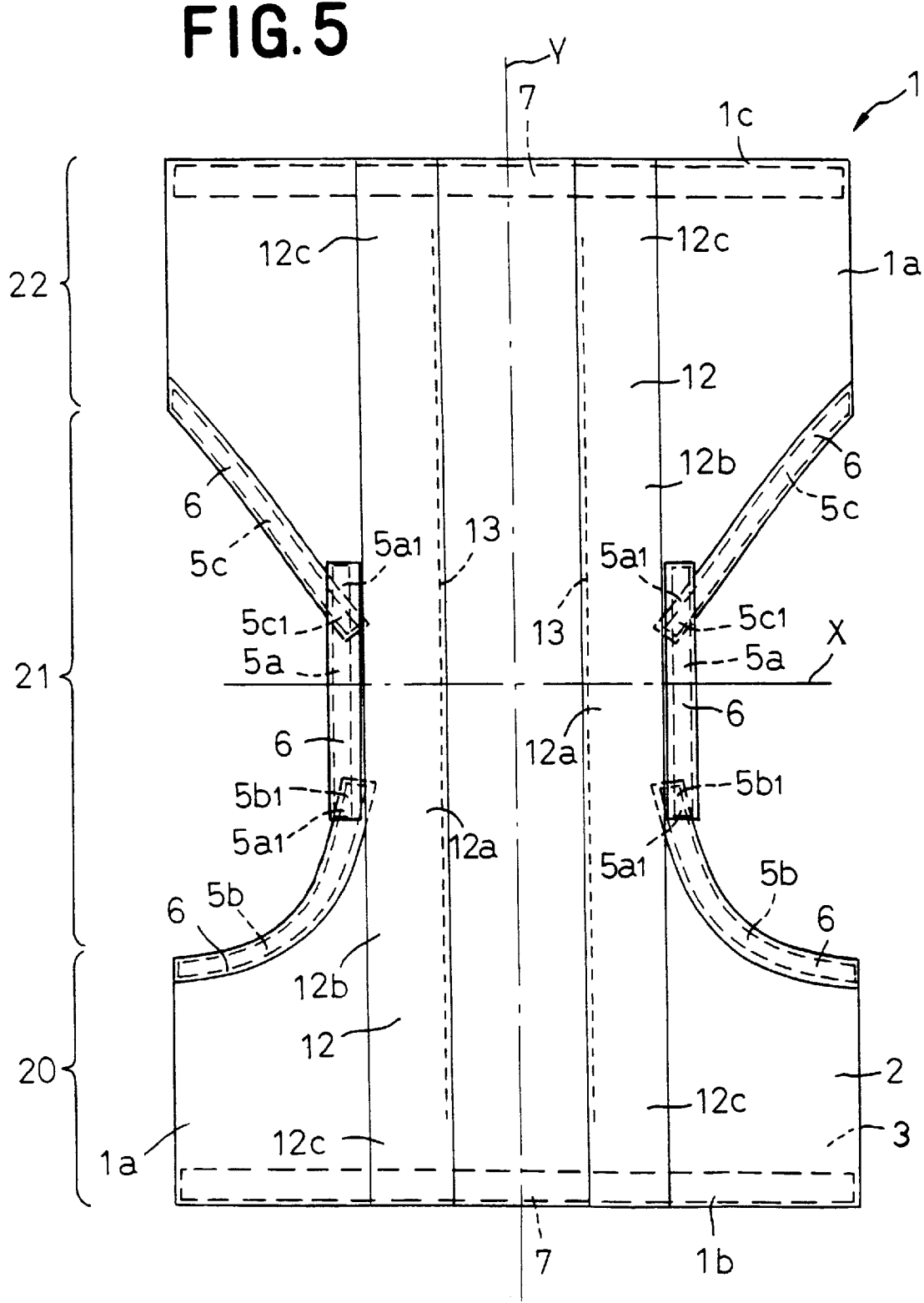

DISPOSABLE GARMENT

BACKGROUND OF THE INVENTION

This invention relates to disposable garments such as disposable diapers of open-type or pants-type, training pants or diaper covers.

Japanese Patent Application Disclosure No. 1987-231005 describes disposable pants comprising a liquid-pervious topsheet, a liquid-impervious backsheet and a liquid-absorbent core extending between these two sheets. Elastic members secured under tension to the sheets of the pants along respective cutouts intended to form a pair of leg-holes, respectively. The elastic members comprise first elastic members lying substantially intermediate portions of the cutouts so as to extend longitudinally of the pants and second and third elastic members extending transversely of the pants from longitudinally opposite ends of the respective first elastic members in continuity with the first elastic members.

During use of the pants movement of the leg-holes over the front thighs is at a maximum, whereas movement over the rear thighs is moderate, and movement in the crotch region is at a minimum. While the Japanese Patent Application Disclosure No. 1987-231005 contains no description about stress of the first-third elastic members, it is concerned that compression marks might be left on the front thighs if the stretch stress is uniform in all the elastic members and this stretch stress is relatively high. Although it will be possible to alleviate the problem of such compression marks by reducing the stretch stress of the elastic members, a rigidity of the core will unacceptably reduce the stretch stress particularly around a crotch region of the pants in which most of excretion is discharged. In this case, the peripheral edges of the leg-holes are apt to be spaced from the wearer's skin and an amount of excretion may leak through this gap formed between the peripheral edges and the wearer's skin.

SUMMARY OF THE INVENTION

It is an object of this invention to provide a disposable garment with improved leg-holes elastic members so that compression marks due to the elastic members may be substantially avoided and a possibility of excretion leakage may be prevented.

According to this invention, there is provided a disposable garment having transversely opposite side edges extending in a longitudinal direction and longitudinally opposite ends extending in a transverse direction which is orthogonal to the longitudinal direction, and leg-hole elastic members which extend in the longitudinal direction being secured under tension to the garment along the transversely opposite side edges.

In the disposable garment according to this invention, the respective sets of the elastic members associated with the leg-holes comprise the first elastic members extending along the transversely opposite side edges of the panel in the longitudinally middle zone of the panel, the second elastic members extending in continuity with the first elastic members toward the front end of the panel and the third elastic members extending in continuity with the first elastic members toward the rear end of the panel. These elastic members previously selected to present their values of stretch stress in the relationship of the first elastic members>the third elastic members>the second elastic members are attached to the panel under tension along the transversely opposite side edges. Such unique arrangement is effective to alleviate a possibility of compression marks left on the wearer's thighs due to the elastic members and simultaneously improve a fit of the panel's side edges around the wearer's thighs so that a concern of excretion leakage may be reliably avoided.

With the diaper of pants-type according to this invention, the elastic members attached to the diaper along the peripheral edges of the leg-holes have the stretch stress which is higher in the crotch region than around the front thighs. As a result, a possibility of compression marks left on the wearer's front thighs can be effectively alleviated and, at the same time, leaking of excretion otherwise possibly occurring in the wearer's crotch region can be reliably avoided.

BRIEF DESCRIPTION OF THE DRAWINGS

FIG. 5 is a plan view showing the diaper of FIG. 4 in its developed state.

DETAILED DESCRIPTION OF THE PREFERRED EMBODIMENTS

Details of a disposable garment according to this invention will be more fully understood from the description of a disposable diaper as one embodiment of this invention given hereunder with reference to the accompanying drawings.

Figure 1:
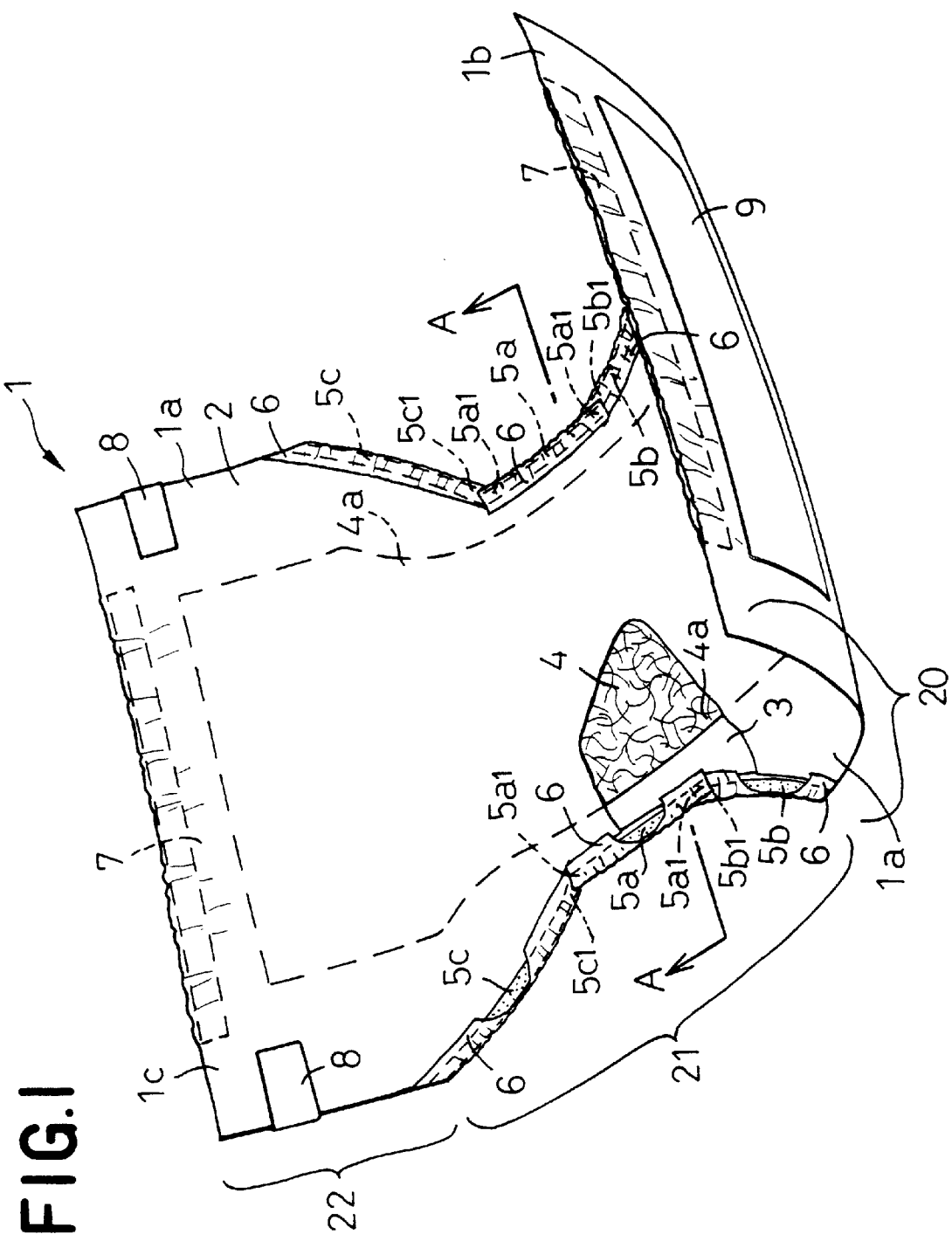
FIG. 1 is a perspective view showing a partially cutaway disposable diaper of open-type as one embodiment of this invention.
Figure 2:
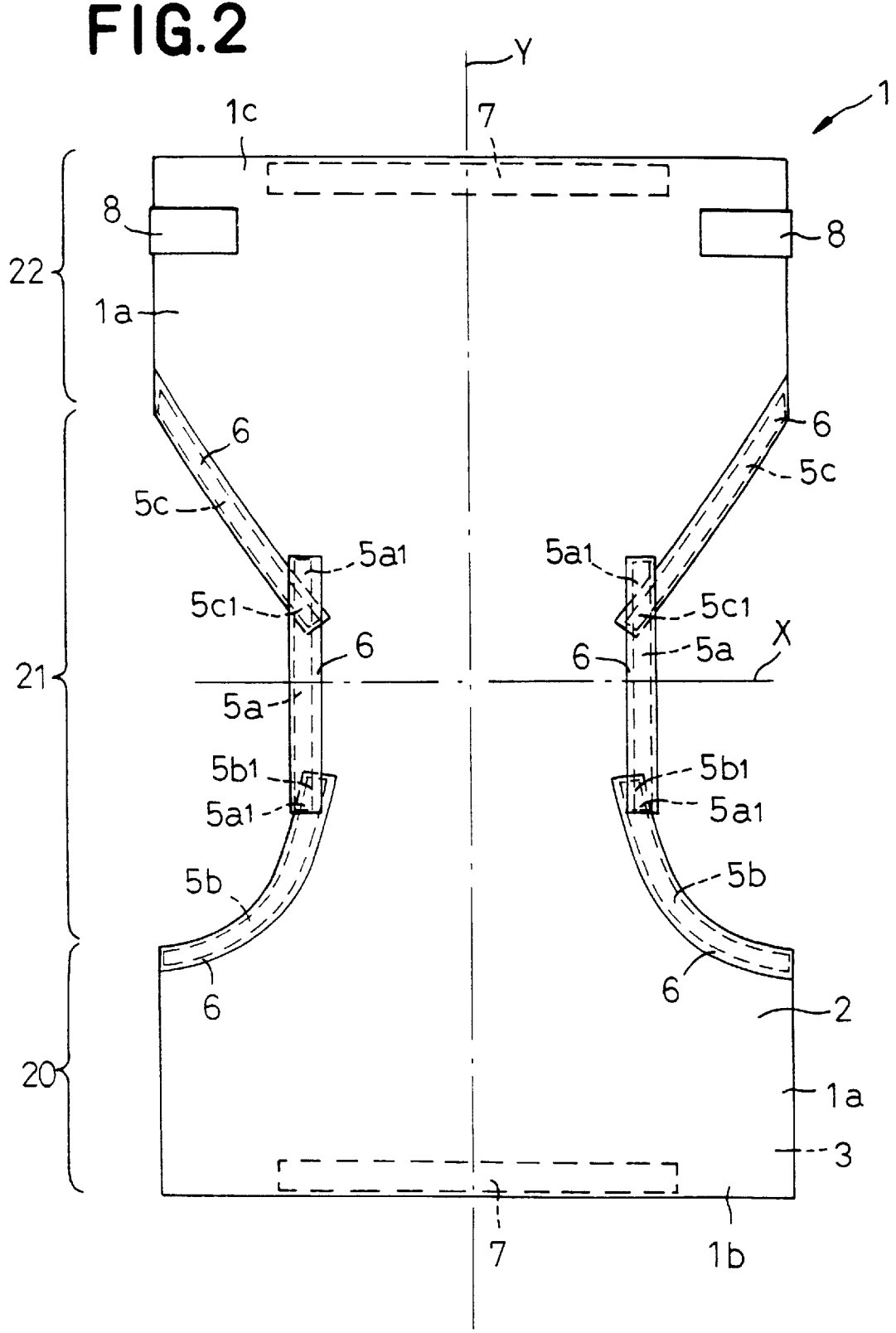
FIG. 2 is a plan view showing the diaper of FIG. 1.

FIG. 1 is a perspective view showing a partially cutaway disposable diaper of open-type as one embodiment of this invention and FIG. 2 is a plan view showing the diaper of FIG. 1. The diaper is formed by a laminated panel 1 comprising a liquid-pervious topsheet 2, a liquid-impervious backsheet 3 and a liquid-absorbent core 4 disposed between the topsheet 2 and the backsheet 3 and joined to the inner surface of at least one of these two sheets 2, 3. The panel 1 is contoured by transversely opposite side edges 1a, 1a extending parallel to each other in a longitudinal direction and longitudinally opposite front and rear ends 1b, 1c extending parallel to each other in a transverse direction which is orthogonal to the longitudinal direction. The panel 1 is hourglass-shaped and has a front waist region 20 extending on the side of the front end 1b, a rear waist region 22 extending on the side of the rear end 1c and a crotch region 21 extending between these front and rear waist regions 20, 22.

As will be apparent from FIG. 2, the transversely opposite side edges 1a, 1a of the panel 1 are curved in the crotch region 21 toward a longitudinal center line Y of the panel 1 bisecting a width of the panel 1. It should be understood that these curves are longer on the side of the front end 1b than on the side of the rear end 1c around a transverse center line X of the panel 1 bisecting a length thereof. In other words, the rear waist region 22 has its area larger than the area of the front waist region 20 in the panel 1.

The panel 1 is provided in the crotch region 21 with leg-hole elastic members 5a, 5b, 5c extending longitudinally of the panel 1 immediately outside the transversely opposite side edges 4a, 4a of the core 4. Each set of these elastic members comprises the first elastic member 5a lying in the longitudinally middle zone of the crotch region 21, the second elastic member 5b lying in the crotch region 21 adjacent the front end 1b of the panel 1 and the third elastic member 5c lying in the crotch region 21 adjacent the rear end 1c of the panel These elastic members 5a, 5b, 5c are secured under tension to strips of nonwoven fabric 6 so as to be covered with these strips of nonwoven fabric 6 and attached together with the strips of nonwoven fabric 6 to the panel 1 under tension directed longitudinally of the panel 1. Longitudinally opposite ends 5a1, 5a1 of the first elastic member 5a overlap the adjacent longitudinal ends 5b1, 5c1 of the second and third elastic members 5b, 5c so that these elastic members 5a, 5b, 5c are successively connected one to another in the longitudinal direction. Values of stretch stress presented by the first~third elastic members 5a, 5b, 5c are adjusted so that a relationship of the first elastic member 5a>the third elastic member 5c>the second elastic member 5b may be established.

Specifically, the first elastic member 5a has a stretch stress of 0.0224~0.2716 gf/mm$^2$, the second elastic member 5b has a stretch stress of 0.0063~0.0429 gf/mm$^2$ and the third elastic member 5c has a stretch stress of 0.0067~0.1291 gf/mm$^2$. These values are those as measured by stretching the first~third elastic members 5a, 5b, 5c respectively secured under tension to the strips of nonwoven fabric 6 and covered therewith at the same stretch ratio before they are attached to the panel 1.

The values of stretch stress presented by the first third~elastic members 5a, 5b, 5c may be selected within the ranges as have been described so far as the previously mentioned relationship of the first elastic member 5a>the third elastic member 5c>the second elastic member 5b is established among the values of stretch stress presented by the respective elastic members 5a, 5b, 5c.

If the values of stretch stress presented by the first~third elastic members 5a, 5b, 5c are less than the respective lower limits thereof, the transversely opposite side edges 1a, 1a of the panel 1 would be apt to be spaced from the wearer's thighs during use of the panel 1 and result in leakage of excretion. The first elastic members 5a, 5a lying in the vicinity of the transversely opposite side edges 4a, 4a would be liable to such problem since the stretch stress of these elastic members 5a, 5a is necessarily reduced by a rigidity of the core 4. Consequently, a deficient stretch stress of the first elastic members 5a, 5a could not ensure a good fit of the transversely side edges 1a, 1a along which the first elastic members 5a, 5a extend around the wearer's thighs and would cause leakage of excretion.

If the values of stretch stress presented by the first~third elastic members 5a, 5b, 5c exceed the respective upper limits thereof, the wearer's thighs would be liable to compression marks due to these elastic members 5a, 5b, 5c particularly on the front thighs having a relatively large movement.

In the front and rear waist regions 20, 22 of the panel 1, there are provided along the longitudinally opposite ends 1b, 1c film-like elastic members 7, 7 associated with a waist-hole extending transversely of the panel 1. These elastic members 7, 7 are disposed between the topsheet 2 and the backsheet 3 and secured under tension to the inner surface of at least one of these two sheets 2, 3. A pair of tape fasteners 8, 8 have their proximal ends attached to the rear waist region 22 of the panel 1 so that these tape fasteners 8, 8 may extend inward transversely of the panel 1 from its transversely opposite side edges 1a, 1a, respectively. The front waist region 20 of the panel 1 is provided on the outer surface of the backsheet 3 with a strip of target tape 9 to which the tape fasteners 8, 8 are anchored.

The panel 1 forms a pair of leg-holes and a waist-hole (not shown) as the tape fasteners 8, 8 are anchored to the strip of target tape 9 by means of pressure-sensitive adhesive applied on the inner surface of free ends of the respective tape fasteners 8, 8. FIG. 1 shows a state in which the leg-hole elastic members 5a, 5b, 5c as well as the waist-hole elastic members 7, 7 have been relieved of the tension and, as a result, gathers have been formed along the transversely opposite side edges 1a, 1a and the longitudinally opposite ends 1b, 1c of the panel 1.

Figure 3:
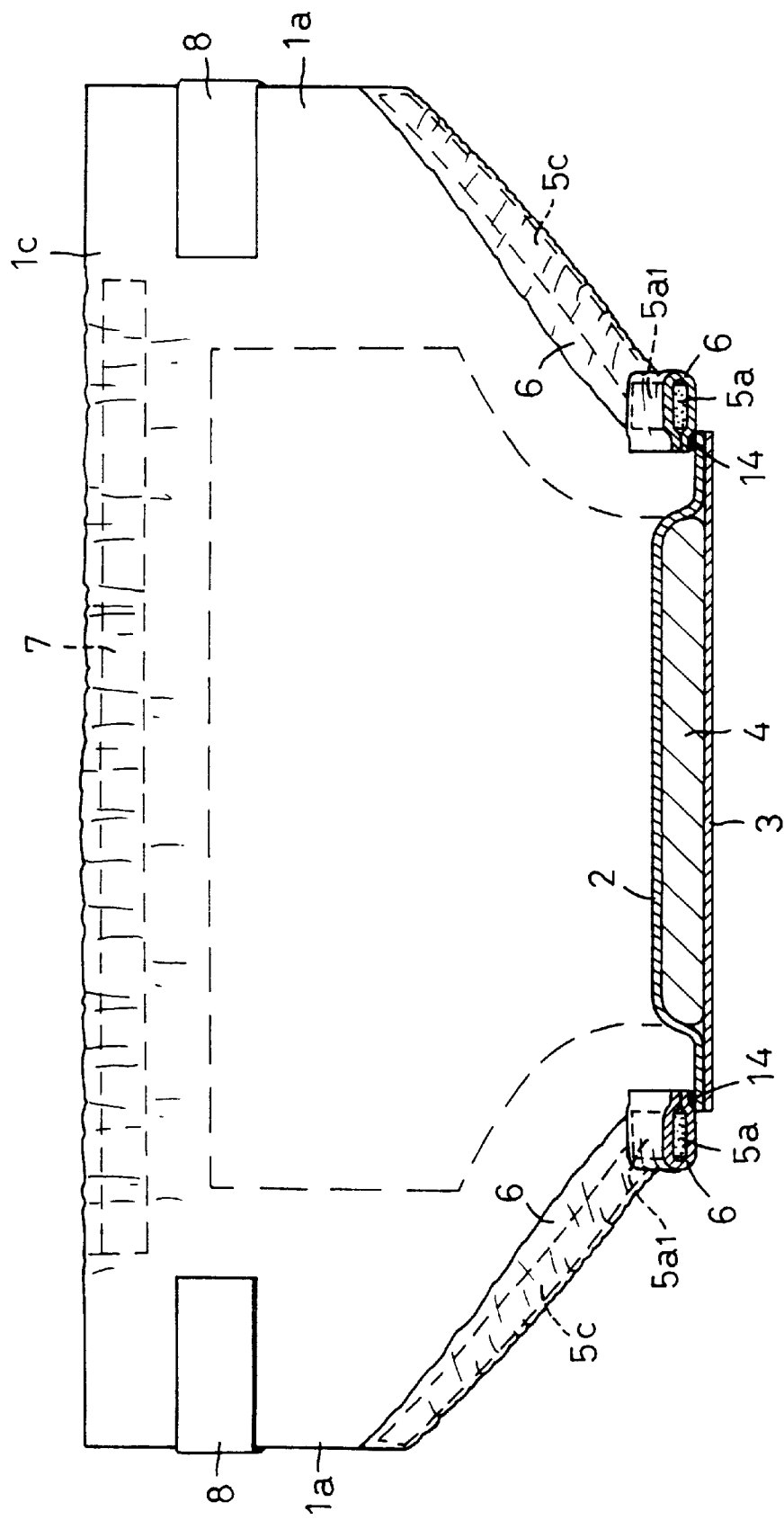
FIG. 3 is a sectional view taken along line A—A in FIG.

FIG. 3 is a sectional view taken along line A—A in FIG. 1. The topsheet 2 and the backsheet 3 extend outward beyond the transversely opposite side edges 4a, 4a of the core 4 and joined to each other. The strips of nonwoven fabric 6 covering the respective elastic members 5a, 5b, 5c are secured to the outer surface of the topsheet 2 by means of adhesive 14.

Figure 4:
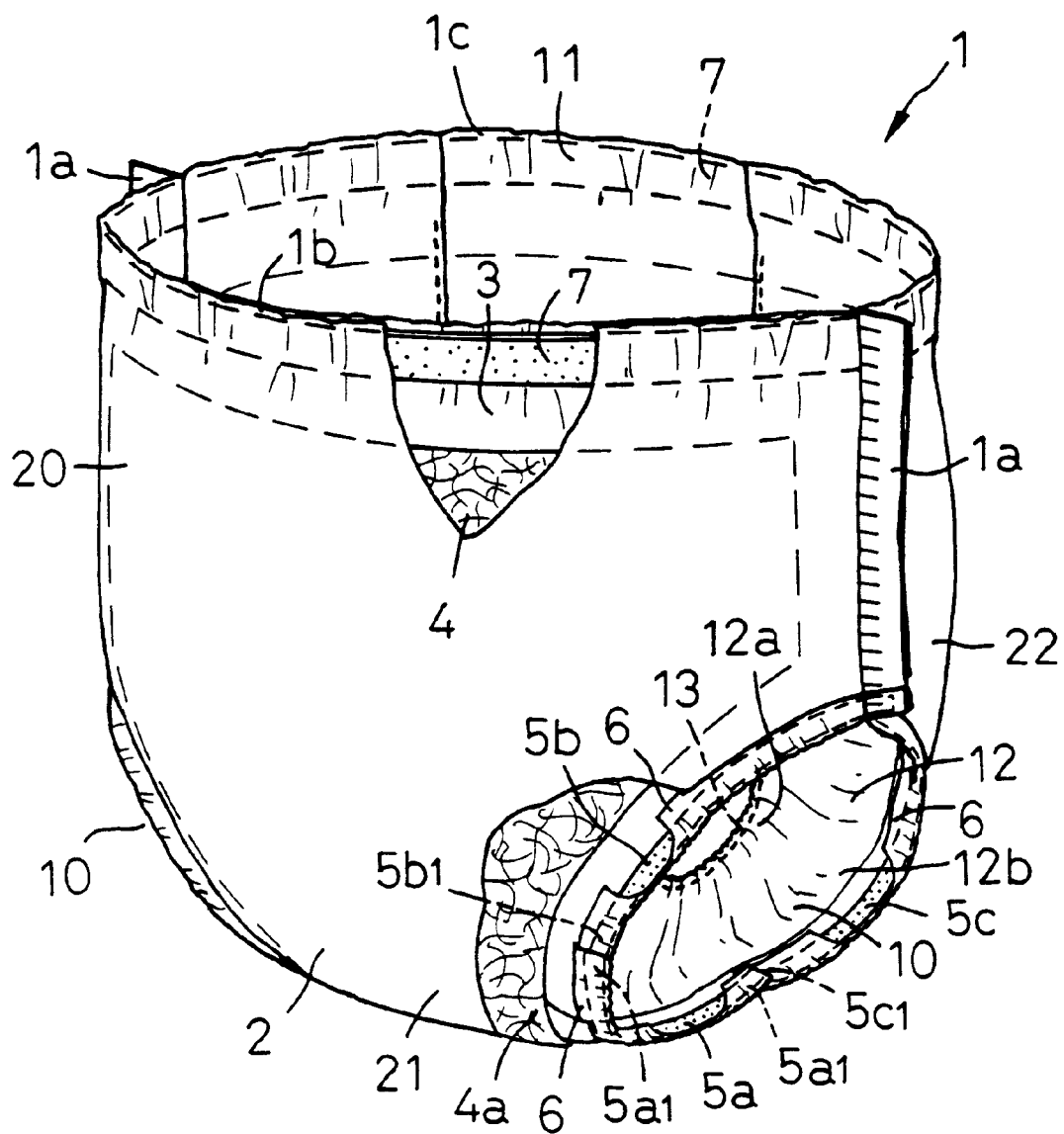
FIG. 4 is a perspective view showing a diaper of pants-type as another embodiment of this invention.

FIG. 4 is a perspective view showing a diaper of pants-type as another embodiment of this invention and FIG. 5 is a plan view showing the diaper of FIG. 4 in its developed state. The diaper according to this embodiment is similar to the panel 1 of FIG. 1 in that the diaper is formed by the laminated panel 1 comprising the topsheet 2, the backsheet 3 and the core disposed between these two sheets 2, 3.

The panel 1 is composed, as viewed longitudinally thereof, of the front waist region 20, the rear waist region 22 and the crotch region 21 extending between these two waist regions 20, 22. The panel 1 is contoured by the transversely opposite side edges 1a, 1a intended to form the pair of leg-holes 10 and the longitudinally opposite ends 1b, 1c intended to form the waist-hole 11. Along peripheral edges of the respective leg-holes 10, the elastic members 5a, 5b, 5c are secured under tension to the panel 1 so as to extend along the entire peripheries of the respective leg-holes 10 and, along peripheral edge of the waist-hole 11, the film-like elastic members 7, 7 are secured under tension to the panel 1 so as to extend along the entire periphery of the waist-hole 11.

As will be apparent from FIG. 5, the transversely opposite side edges 1a, 1a of the panel 1 are curved in the crotch region 21 toward a longitudinal center line Y of the panel 1 bisecting a width of the panel 1. These curves are longer on the side of the front end 1b than on the side of the rear end 1c around a transverse center line X of the panel 1 bisecting a length thereof. In other words, the rear waist region 22 has its area larger than the area of the front waist region 20 in the panel 1.

The panel 1 is provided in the crotch region 21 with leg-hole elastic members 5a, 5b, 5c extending along the transversely opposite side edges 1a, 1a. Each set of these elastic members comprises the first elastic member 5a lying substantially in the longitudinally middle zone of the crotch region 21, the second elastic member 5b lying in the crotch region 21 adjacent the front end 1b of the panel 1 and the third elastic member 5c lying in the crotch region 21 adjacent the rear end 1c of the panel 1.

These elastic members 5a, 5b, 5c are secured under tension to strips of nonwoven fabric 6 so to be covered with these strips of nonwoven fabric 6 and attached together with the strips of nonwoven fabric 6 to the panel 1 with tension directed longitudinally of the panel 1. Longitudinally opposite ends $5a_1$, $5a_1$ of the first elastic member 5a overlap the adjacent longitudinal ends $5b_1$, $5c_1$ of the second and third elastic members 5b, 5c so that these elastic members 5a, 5b, 5c are successively connected one to another in the longitudinal direction. Values of stretch stress presented by the first~third elastic members 5a, 5b, 5c are adjusted so that a relationship of the first elastic member 5a>the third elastic member 5c>the second elastic member 5b may be established.

Specifically, the first elastic element 5a has a stretch stress of 0.0224~0.2716 gf/mm$^2$, the second elastic member 5b has a stretch stress of 0.0063~0.0429 gf/mm$^2$ and the third elastic member 5c has a stretch stress of 0.0067~0.1291 gf/mm$_2$. These values are those as measured by stretching the first~third elastic members 5a, 5b, 5c respectively bonded with tension to the strips of nonwoven fabric 6 and covered therewith at a same stretch ratio before they are attached to the panel 1.

According to this embodiment, the panel 1 is provided with a pair of barrier cuffs 12 extending longitudinally of the panel 1. Each of the cuffs 12 has a free side edge 12a joined neither to the topsheet 2 nor to the backsheet 3, a fixed side edge 12b opposed to the free side edge 12a and longitudinally opposite ends 12c, 12c lying on the longitudinally opposite ends 1b, 1c of the panel 1 and joined to the outer surface of the topsheet 2 as they are fixedly collapsed inwardly of the panel 1. The fixed side edge 12b lies between the associated side edge 4a of the core 4 and the associated set of the elastic members 5a, 5b, 5c and is secured to the outer surface of the topsheet 2.

A portion of the cuff 12 extending outward from its fixed side edge 12b transversely of the panel 1 and the longitudinally opposite ends 12c are shaped so that the cuff 12 does not extend beyond the outer contour of the backsheet 3. The cuff 12 is provided along its free side edge 12a with a longitudinally extending elastic member 13 secured under tension to the free side edge 12a so that this elastic member 13 may be covered with the free side edge 12a of this cuff 12.

The panel 1 is longitudinally folded along the transverse center line X with the topsheet 2 inside and then the front and rear waist regions 20, 22 are joined together along the transversely opposite side edges a, 1a of these waist regions 20, 22 to form the diaper of open-type. The elastic members 5a, 5b, 5c have their stretch stresses previously selected to establish the aforementioned relationship . The values of the stretch stress presented by the respective elastic members previously adjusted in the relationship of the first elastic member 5a>the third elastic member 5c>the second elastic member 5b alleviate a possibility of compression marks left on the front thighs due to the second elastic members 5b and prevents any amount of excretion from leaking around the crotch region due to the first elastic members 5a which may be affected by a rigidity of the core 4.

A liquid-pervious sheet, preferably a liquid-pervious but hydrophobic sheet such as a nonwoven fabric or a porous plastic film may be used as stock material for the topsheet 2. A liquid-impervious plastic film or a laminate consisting of such plastic film and hydrophobic nonwoven fabric, preferably a breathable but liquid-impervious sheet may be used as stock material for the backsheet 3. The cuffs 12 may be formed by a breathable nonwoven fabric, preferably by a breathable but liquid-impervious nonwoven fabric. The nonwoven fabric used for this purpose may be selected from a group including an air-through nonwoven fabric, a spun bond nonwoven fabric, a spun lace nonwoven fabric and a melt blown nonwoven fabric. The core 4 may be formed by compressing a mixture of fluff pulp and highly absorptive polymer grains to a desired thickness and entirely covering this with a water-pervious sheet (not shown) such as tissue paper.

Elastomer such as synthetic rubber or natural rubber may be used as stock material for the elastic members 5a, 5b, 5c. These elastic members 5a, 5b, 5c may be of film-like or thread-like form. Joining of the various components such as the core 4, the elastic members 5a, 5b, 5c, the sheets 2, 3 and the cuffs 12 may be carried out using suitable adhesive such as hot melt adhesive or pressure-sensitive adhesive or heat-sealing technique.

The feature that the respective elastic members 5a, 5b, 5c are covered with the strips of nonwoven fabric is particularly important for this invention. Specifically, these strips of nonwoven fabric protect the wearer's skin from direct contact with the elastic members 5a, 5b, 5c and thereby from having an eruption and/or feeling of incompatibility even if the elastic members 5a, 5b, 5c are attached to the outer surface of the topsheet 2. It is also possible to secure the elastic members 5a, 5b, 5c under tension to the outer surface of the backsheet 3 or to dispose these elastic members having no strip of nonwoven fabric covering them between the topsheet 2 and the backsheet 3 and to secure them under tension to at least one of these two sheets 2, 3.

The longitudinally opposite ends $5a_1$, $5a_1$ may be also connected with the respective longitudinal ends $5b_1$, $5c_1$, of the elastic members 5b, 5c in end-to-end fashion instead of overlapping them one upon another. By longitudinally connecting the elastic members 5a, 5b, 5c in this end-to-end fashion, it is possible to avoid a difference in level necessarily occurring when the longitudinally opposite ends $5a_1$, $5a_1$ of the elastic members 5a overlap the respective longitudinal ends $5b_1$, $5c_1$, of the elastic members 5b, 5c. With an advantageous consequence, it is not concerned that the elastic members 5a, 5b, 5c might give the wearer's skin no feeling of compatibility during use of the diaper. The elastic members 5a, 5b, 5c may extend into the front and rear waist regions 20, 22 beyond the crotch region 21, if desired.

What is claimed is:

1. A disposable garment having transversely opposite side edges extending in a longitudinal direction and longitudinally opposite front and rear ends extending in a transverse direction which is orthogonal to said longitudinal direction, leg-hole elastic members which extend in said longitudinal direction being secured under tension to said garment along said transversely opposite side edges, wherein:

said leg-hole elastic members comprise first elastic members extending along said transversely opposite side edges in a longitudinally middle zone of said garment, second elastic members extending in continuity with said first elastic members toward said front end and third elastic members extending in continuity with said first elastic members toward said rear end, and a stretch stress of said first elastic members>a stretch stress of said third elastic members>a stretch stress of said second elastic members.

2. The disposable garment according to claim 1, wherein said first, second and third elastic members are respectively covered with strips of nonwoven fabric and secured under tension thereto and wherein said first elastic members have a stretch stress of $0.0224 \sim 0.2716$ gf/mm$^2$, said second elastic members have a stretch stress of $0.0063 \sim 0.0429$ gf/mm$^2$ and said third elastic members have a stretch stress of $0.0067 \sim 0.1291$ gf/mm$^2$ as measured by stretching said first, second and third elastic members respectively secured under tension to the strips of nonwoven fabric and covered therewith at the same stretch ratio before they are attached to said garment.

3. The disposable garment according to claim 1, wherein longitudinally opposite ends of said first elastic members overlap adjacent longitudinal ends of said second and third elastic members.

4. The disposable garment according to claim 1, wherein said garment is formed by a laminated panel comprising a liquid-pervious topsheet, a liquid-impervious backsheet and a liquid-absorbent core disposed between said topsheet and said backsheet wherein said panel is composed, in said longitudinal direction, of a front waist region, a rear waist region and a crotch region extending between said front and rear waist regions and curved inwardly toward a longitudinal center line of said panel and wherein said first, second and third elastic members are attached to said panel along transversely opposite side edges of said crotch region.

* * * * *